United States Patent
Phillips et al.

(10) Patent No.: US 10,687,852 B2
(45) Date of Patent: *Jun. 23, 2020

(54) SEPARABLE INSTRUMENT DRIVER HANDLE

(71) Applicant: Symmetry Medical Manufacturing, Inc., Warsaw, IN (US)

(72) Inventors: Alton Phillips, Warsaw, IN (US); John Conley, Silver Lake, IN (US)

(73) Assignee: Symmetry Medical Manufacturing, Inc., Warsaw, IN (US)

(*) Notice: Subject to any disclaimer, the term of this patent is extended or adjusted under 35 U.S.C. 154(b) by 657 days.

This patent is subject to a terminal disclaimer.

(21) Appl. No.: 14/853,332

(22) Filed: Sep. 14, 2015

(65) Prior Publication Data

US 2017/0071631 A1    Mar. 16, 2017

(51) Int. Cl.
*A61B 17/56*      (2006.01)
*A61B 17/00*      (2006.01)

(52) U.S. Cl.
CPC ...... *A61B 17/56* (2013.01); *A61B 2017/0046* (2013.01); *A61B 2017/00429* (2013.01); *A61B 2017/00477* (2013.01)

(58) Field of Classification Search
CPC ............ A61B 17/56; A61B 2017/0046; A61B 2017/00477; A61B 2017/00464; A61B 2017/00442; A61B 2017/00429; A61B 2017/00433; A61F 2002/4624

See application file for complete search history.

(56) References Cited

U.S. PATENT DOCUMENTS

| | | |
|---|---|---|
| 2,090,885 A | 8/1937 | Clark |
| 5,643,271 A | 7/1997 | Sederholm et al. |
| 5,772,436 A | 6/1998 | Matsui et al. |
| 7,326,198 B2 | 2/2008 | Desarzens et al. |
| 7,537,597 B2 | 5/2009 | Salazar et al. |
| 7,611,515 B2 | 11/2009 | Wolford et al. |
| 7,615,053 B2 * | 11/2009 | McKinley .......... A61B 17/1611 606/83 |
| 7,699,852 B2 * | 4/2010 | Frankel ............. A61B 17/1655 606/92 |
| 7,780,669 B2 | 8/2010 | Lechot et al. |
| 7,819,296 B2 | 10/2010 | Hueil et al. |
| 7,976,548 B2 | 7/2011 | Burgi et al. |
| 8,052,690 B2 | 11/2011 | Berthusen et al. |
| 8,323,284 B2 | 12/2012 | Ferreira |
| 8,348,959 B2 | 1/2013 | Wolford et al. |
| 8,398,642 B2 | 3/2013 | Weekes |
| 8,403,931 B2 | 3/2013 | Sidebotham et al. |
| 8,806,973 B2 | 8/2014 | Ross et al. |
| 8,834,484 B2 | 9/2014 | Kehres et al. |
| 8,900,246 B2 | 12/2014 | Lashure et al. |
| 2004/0172036 A1 | 9/2004 | Dye |

(Continued)

*Primary Examiner* — Anu Ramana
(74) *Attorney, Agent, or Firm* — Taylor IP, P.C.

(57) ABSTRACT

An orthopaedic driver handle including a drivetrain having a driving end and a driven end opposite the driving end and defining a longitudinal axis, and a separable housing covering at least a portion of the drivetrain. The separable housing includes a first portion and a second portion separably connected to the first portion such that sliding the first portion relative to the second portion in a direction of the longitudinal axis unlocks the first portion from the second portion.

7 Claims, 7 Drawing Sheets

(56) References Cited

U.S. PATENT DOCUMENTS

2005/0075660 A1*  4/2005  Chu ................. A61B 17/06109
                                              606/190
2009/0088757 A1   4/2009  Tulkis
2012/0184946 A1*  7/2012  Price .............. A61B 17/320092
                                              606/1
2013/0261632 A1  10/2013  Livorsi et al.

* cited by examiner

SEPARABLE INSTRUMENT DRIVER HANDLE

BACKGROUND OF THE INVENTION

1. Field of the Invention

The present invention relates to orthopaedic instrument handles, and, more particularly, to separably connected orthopaedic driver handles.

2. Description of the Related Art

When performing orthopaedic procedures, orthopaedic drivers are often used to connect a surgical instrument, such as a reamer head, to a power drill or other rotating element. Typical orthopaedic drivers include a shank that couples with the rotating element and a drive shaft to transmit rotation from the shank to the surgical instrument. Using reaming as an example of use, the reamer head connected to the orthopaedic driver is used to cut a bone in order to prepare it to receive the stem of an orthopaedic implant. A reamer head typically has a convex shape with a peripheral surface that has a plurality of radially extending teeth for cutting the bone. Generally the bone is cut into a hemispherical shape as the reamer cuts deeper into the bone in an axial direction. Much of the size and shape of the cut depends on the configuration of the reamer head, which ultimately leads to whether the implant will be successfully received.

Angled orthopaedic drivers have become more popular by furthering the endeavor of making joint replacement surgery less invasive. In angled orthopaedic drivers, the drive shaft typically defines one axis and the driven instrument defines another axis which is oriented at an angle relative to the drive shaft. Angled orthopaedic drivers allow the user to obtain the desired angle for reaming or attaching bone screws into an implant without necessitating a more invasive and less ergonomic approach. Angled configurations of orthopaedic drivers permit the surgical instrument to operate using a smaller incision, in some instances less than 50 mm for a total hip arthroplasty (THA).

Orthopaedic drivers should be sterilized prior to use in order to lower the risk of infection during a surgical procedure. Since the cost of producing orthopaedic drivers is typically too high to produce the driver as a disposable tool, orthopaedic drivers are frequently reused for multiple orthopaedic surgeries. This creates a great need for durability and a more easily sterilized orthopaedic driver. Yet, prior to the sterilization process the orthopaedic driver must be disassembled and meticulously cleaned to remove contaminating matter, making ease of access to contaminated surfaces of the orthopaedic driver a paramount concern. Unfortunately, cleaning orthopaedic drivers is generally an arduous process, particularly when cleaning the intricate components that secure the housing around the drive shaft and rotating element. Generally, orthopaedic surgery causes considerable contamination of the surgical instrument and the orthopaedic driver holder. Often, tissue debris and coagulated blood can become trapped in the crevices within the orthopaedic driver handle, making the cleaning process especially burdensome. The adverse issues of the cleaning process are exacerbated when the orthopaedic driver has more moving parts associated therewith. An orthopaedic driver handle with a greater number of connecting parts increases the likelihood that debris will collect therein.

What is needed in the art is a cost effective orthopaedic driver handle that can be more easily sterilized.

SUMMARY OF THE INVENTION

The present invention provides an orthopaedic driver handle that includes a drivetrain and a separable housing that has a first portion and a second portion such that distally sliding the first portion relative to the second portion unlocks the first portion from the second portion.

The invention in one form is directed to an orthopaedic driver handle that includes a drivetrain having a driving end and a driven end opposite the driving end and defining a longitudinal axis, and a separable housing covering at least a portion of the drivetrain. The separable housing includes a first portion and a second portion separably connected to the first portion, wherein sliding the first portion relative to the second portion in a direction of the longitudinal axis unlocks the first portion from the second portion.

The invention in another form is directed to a method of sanitizing an orthopaedic driver handle that includes providing the orthopaedic driver handle which includes a drivetrain having a driving end and a driven end opposite the driving end and defining a longitudinal axis and a separable housing covering at least a portion of the drivetrain. The separable housing includes a first portion and a second portion separably connected to the first portion, wherein sliding the first portion relative to the second portion in a direction of the longitudinal axis unlocks the first portion from the second portion. The method further includes sliding the first portion relative to the second portion in the direction of the longitudinal axis to unlock the separable housing, separating the first portion from the second portion, sterilizing at least one of the drivetrain, the first portion of the separable housing and the second portion of the separable housing, and relocking the separable housing by aligning the first portion with the second portion of the separable housing and sliding the first portion relative to the second portion.

An advantage of the present invention is the orthopaedic driver handle includes relatively few parts and can be quickly disassembled and reassembled, making the process of sterilization less burdensome.

Another advantage is the annular collar expeditiously and intuitively mates to the first portion and the second portion of the separable housing to prevent the separable housing from unlocking

BRIEF DESCRIPTION OF THE DRAWINGS

The above-mentioned and other features and advantages of this invention, and the manner of attaining them, will become more apparent and the invention will be better understood by reference to the following description of an embodiment of the invention taken in conjunction with the accompanying drawings, wherein.

Corresponding reference characters indicate corresponding parts throughout the several views. The exemplification set out herein illustrates an embodiment of the invention and such exemplification is not to be construed as limiting the scope of the invention in any manner.

DETAILED DESCRIPTION OF THE INVENTION

Figure 1:
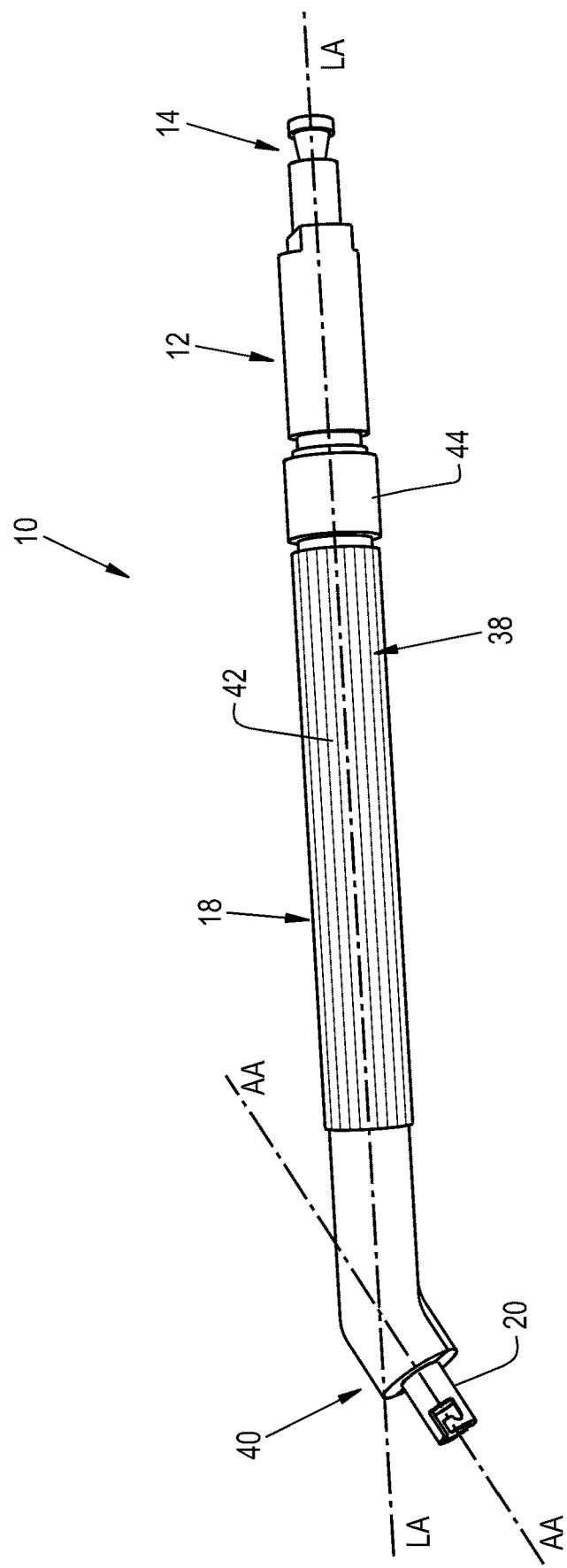
FIG. 1 is a perspective view of an embodiment of an orthopaedic driver handle according to the present invention.

Referring now to the drawings, and more particularly to FIG. 1, there is shown an embodiment of an orthopaedic driver handle 10 according to the present invention that generally includes a drivetrain 12, which has a driven end 14 opposite a driving end 16 and defines a longitudinal axis LA, and a separable housing 18 that partially covers the drivetrain 12.

Figure 2:
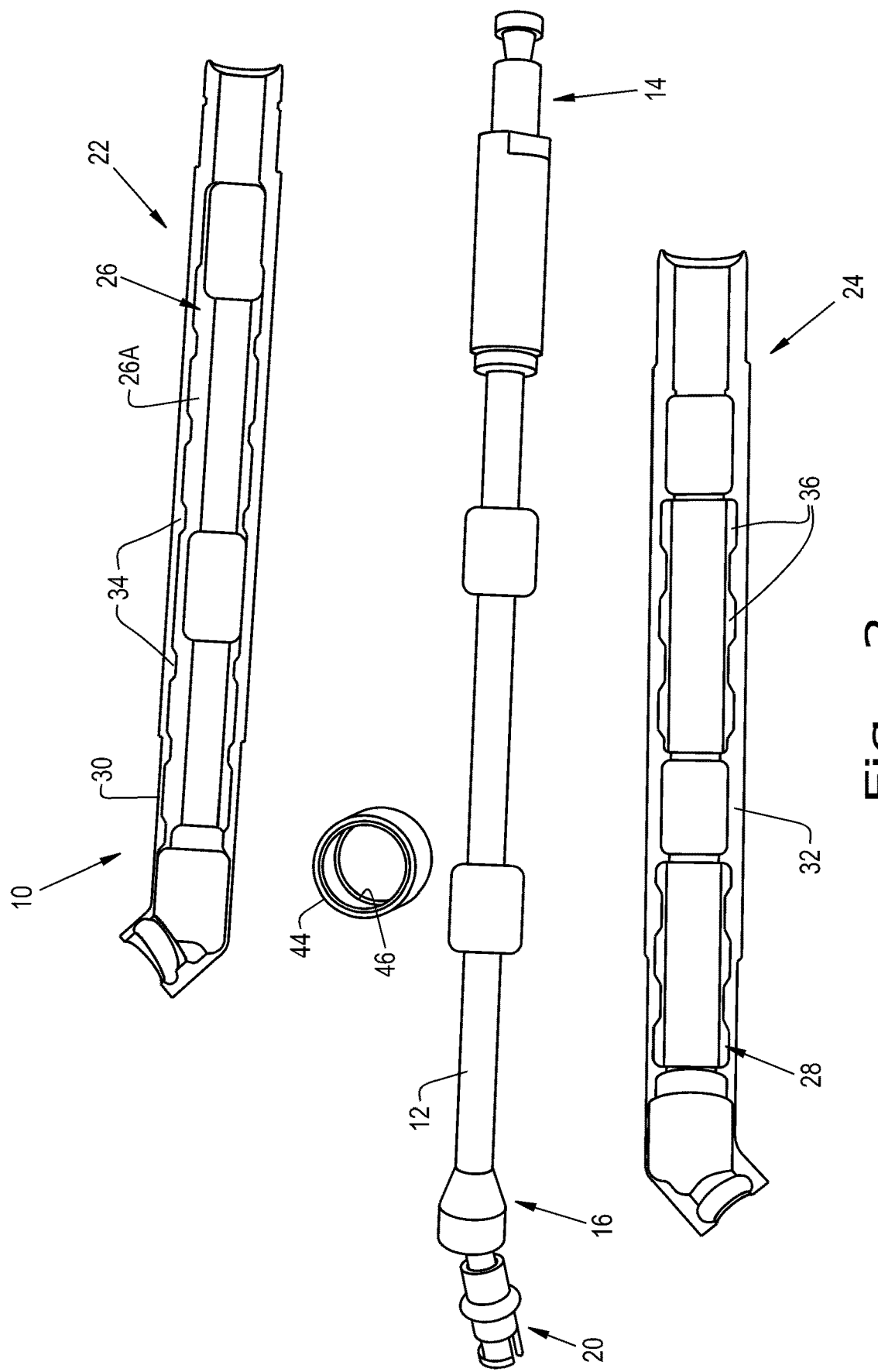
FIG. 2 is an exploded view of the orthopaedic driver handle shown in FIG. 1 with the housing removed.

Referring now to FIG. 2, the orthopaedic driver handle 10 is shown disassembled to better illustrate the other components of the driver handle 10. The driven end 14 of the drivetrain 12 may be a shank, or another connecting member, which connects to a source of rotational motion, such as a power drill (not shown). The driving end 16 may be rotatably connected to an instrument connector 20 that connects to an orthopaedic end effector, such as a reamer head (not shown). While the driving end 16 is shown as being flared, any configuration of a driving end can be chosen that can rotatably couple to an instrument connector 20 and/or end effector. In operation, as the power drill rotates, the drivetrain 12 will transfer the rotational motion from the drill to the orthopaedic end effector. The longitudinal axis LA is the axis about which the drivetrain 12 rotates, as shown in FIG. 1.

Figure 3:
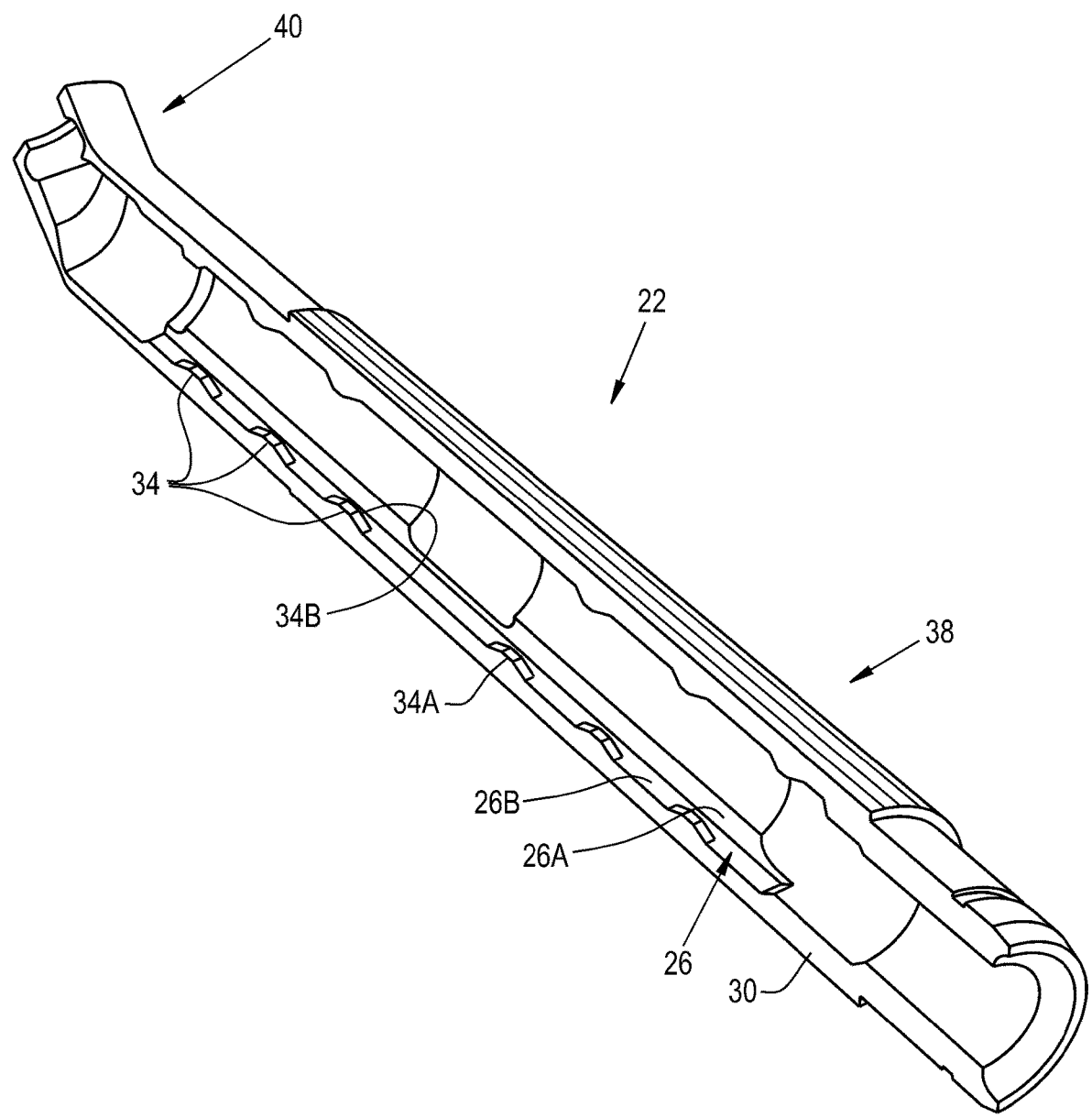
FIG. 3 is a perspective view of the first portion of the separable housing shown in FIG. 2.
Figure 4:
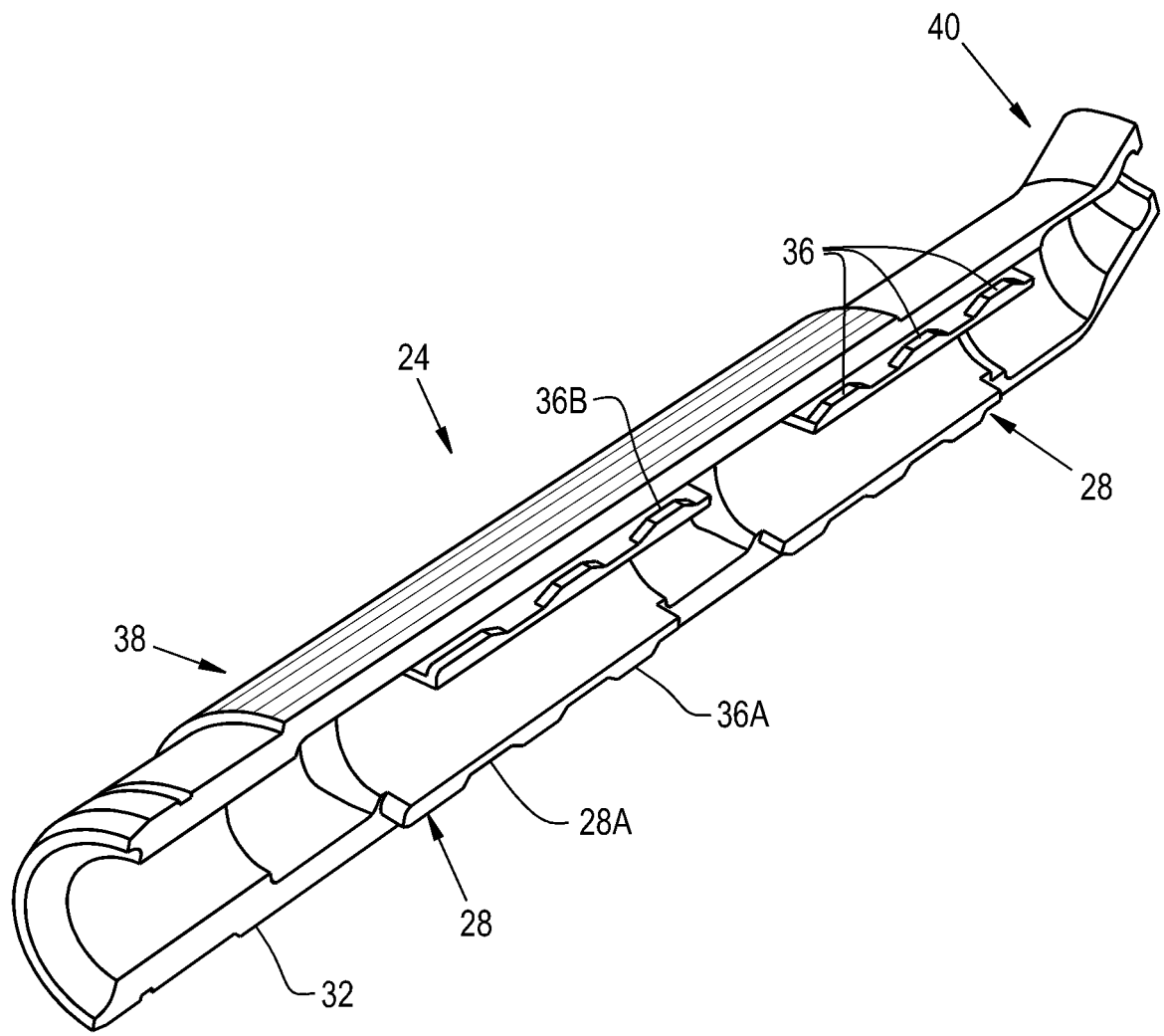
FIG. 4 is a perspective view of the second portion of the separable housing shown in FIG. 2.

Referring now to FIGS. 2-4, there is shown the separable housing 18 according to the present invention that generally includes a first portion 22 and a second portion 24. As can be surmised, the separable housing 18 can include more than two portions, i.e. three portions, four portions, etc. The first portion 22 can have locking features in the form of grooves 26 that correspond with locking features in the form of tabs 28 on the second portion 24. As shown in detail in FIGS. 3 and 4 respectively, the grooves 26 can be formed adjacent to the circumferential edge 30 of the first portion 22, and the tabs 28 can be formed adjacent to the circumferential edge 32 of the second portion 24. The grooves 26 and tabs 28 are shown to be machined from their respective portions 22 and 24. Yet, as can be surmised the grooves 26 and tabs 28 may be formed of a different material and/or be individually attached as separate members. The grooves 26 and tabs 28 may also simply be in the form of one groove and one corresponding tab.

The grooves 26 each have an inner wall 26A and a bottom surface 26B. The inner wall 26A of the grooves 26 can extend parallel to the circumferential edge 30 of the first portion 22. The bottom surface 26B of the grooves 26 can support at least one ramped feature 34 that has an outer surface 34A and an inner surface 34B. Each respective outer surface 34A of the ramped features 34 can be aligned flush with the circumferential edge 30. As shown in FIG. 3, there are multiple ramped features 34 that are spaced to create openings there between along the bottom surface 26B adjacent the peripheral edge of the grooves 26.

The tabs 28 can extend outwardly from the circumferential edge 32 of the second portion 24. The tabs 28 have an outer surface 28A that is parallel to the circumferential edge 32. The tabs 28 can include at least one locking protrusion 36 that has an outer surface 36A and an inner surface 36B. Each outer surface 36A of the locking protrusion 36 can align flush with the outer surface 28A of the tabs 28. As shown in FIG. 4, the tabs 28 can have a series of locking protrusions 36 that form an appearance of alternating plateaus and valleys. The locking protrusions 36 are disposed to pass between the ramped features 34 and fit within the grooves 26 of the first portion 22.

Additionally, the first portion 22 and the second portion 24 can each include an elongated straight region 38 and an angled region 40. The elongated region 38 can be substantially parallel to the longitudinal axis LA. The elongated region 38 may include spaces to accommodate the drivetrain 12, bushings and/or bearings. The angled region 40 defines an angled axis AA that is oriented at a transverse angle relative to the longitudinal angle LA, as shown in FIG. 1. The angled region 40 may include spaces to accommodate the instrument connector 20, bushings and or bearings. When the first and second portions 22, 24 are joined, each respective elongated region 38 can cover the majority of the rotating parts of the drivetrain 12 and each respective angled region 40 can partially cover the instrument connector 20.

The separable housing 18 may include a gripping feature in the form of a plurality of scallops 42 on the outer surface of the separable housing 18 for improving a user's tactile grip during the surgical procedure. The scallops 42, as shown in FIG. 1, can be parallel to the longitudinal axis LA. The scallops 42 can be created by forming valleys between two ridges in the outer surface of the separable housing 18. However, the scallops 42 can be oriented at an angle transverse to the longitudinal axis LA and may be formed by any pattern of undulations. Further, the gripping feature may be formed by a gripping texture or an abrasion on the outer surface of the separable housing 18.

The orthopaedic driver handle 10 may also include a first locking member in the form of an annular collar 44 that is mated to the exterior of the separable housing 18, as shown in FIG. 1. The annular collar 44 may include a second locking member in the form of a spring-loaded element, such as a spring pin 46 (shown in FIG. 2), to keep the annular collar 44 from slipping off of the separable housing 18. The second locking member may mate at a specified notch and/or ridge 48 (shown in FIG. 5) formed in the exterior surface of the separable housing 18 adjacent the driven end 16, or at any desired location along the exterior of the separable housing 18. The second locking member may also be in the form of pins, clasps, threads and/or fasteners.

To assemble the orthopaedic driver handle 10, the first and second portions 22, 24 are aligned so that the locking protrusions 36 of the tabs 28 can pass between the spaced ramped features 34 along the bottom surface 26A of the grooves 26. The first and second portions 22, 24 are then brought together so that their respective circumferential edges 30, 32 touch each other. At this point, the outer surface 36A of the locking protrusions 36 abut the inner wall 26A of the grooves 26, and the outer surface 34A of the ramped features 34 abut the circumferential edge 32 of the second portion 24. The locking protrusions 36 fit substantially within the grooves 26, thereby being housed within the first portion 22. To lock the first portion 22 and second portion 24, the first portion 22 is slid in a direction of the longitudinal axis LA. Once the first portion 22 is slid into place, each inner surface 36B of the locking protrusions 36 abuts the corresponding inner surface 34B of the ramped features 34. Now, since the grooves 26 and tabs 28 have been interlocked, the first portion 22 and the second portion 24 cannot separate laterally outward and the first and second portions 22, 24 are rotationally locked together. Then, the annular collar 44 is mated to the first and second portions 22, 24 of the separable housing 18, which interferes with sliding of the first and second portions 22, 24 relative to one another and prevents them from unlocking.

Figure 5:
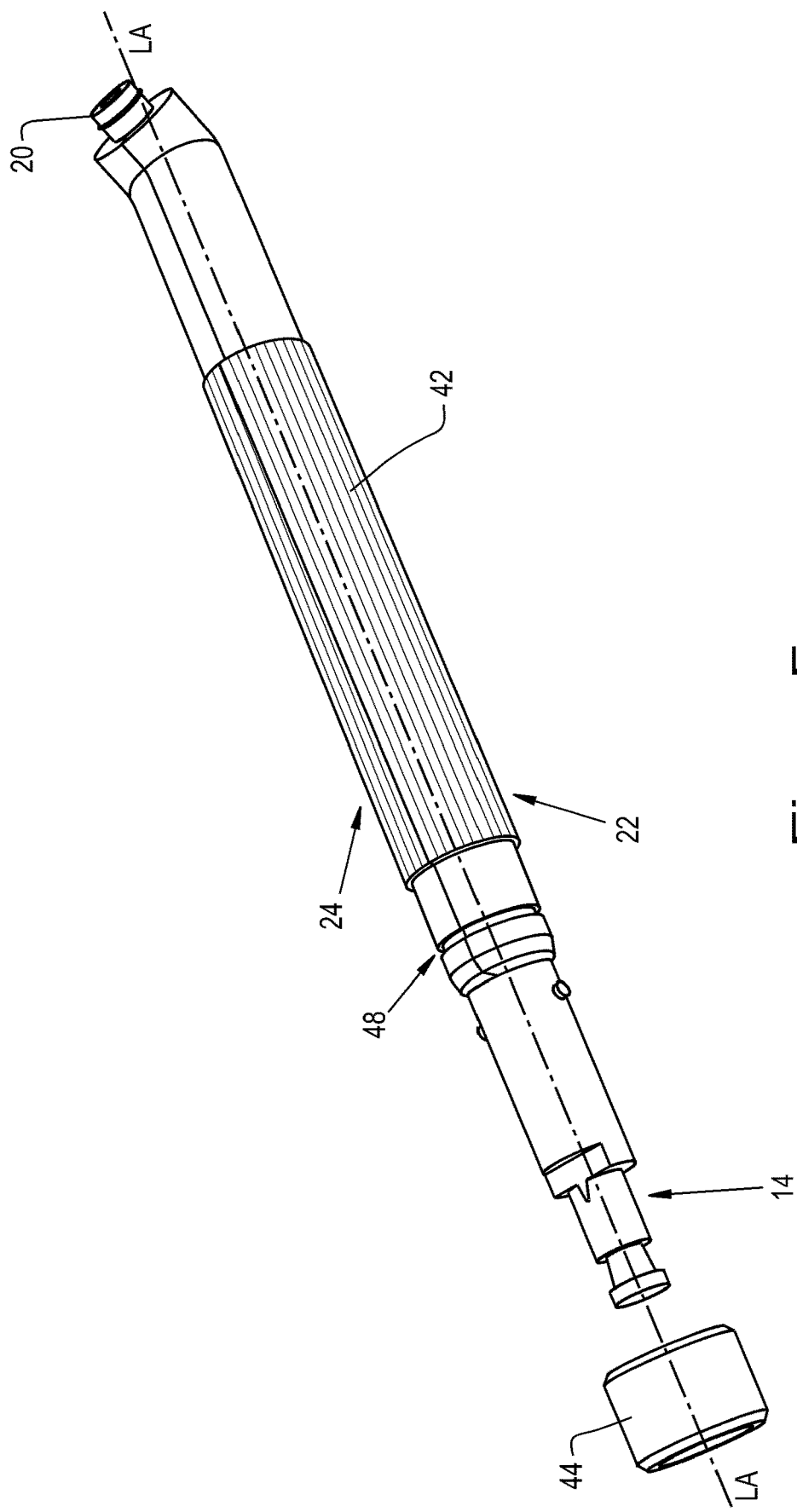
FIGS. 5-7 are perspective views of the orthopaedic driver handle according to the present invention illustrating the disassembly of the orthopaedic driver handle.
Figure 6:
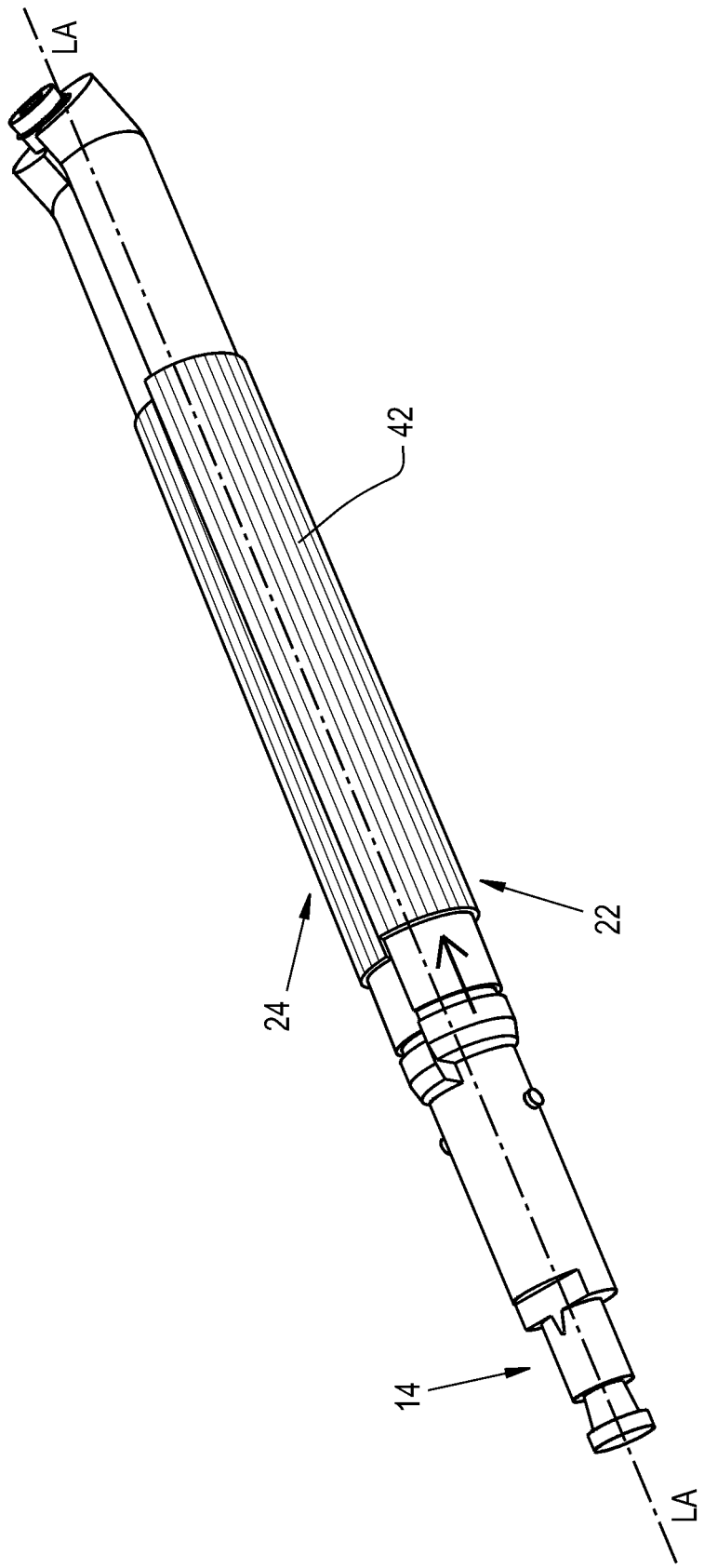
Figure 7:
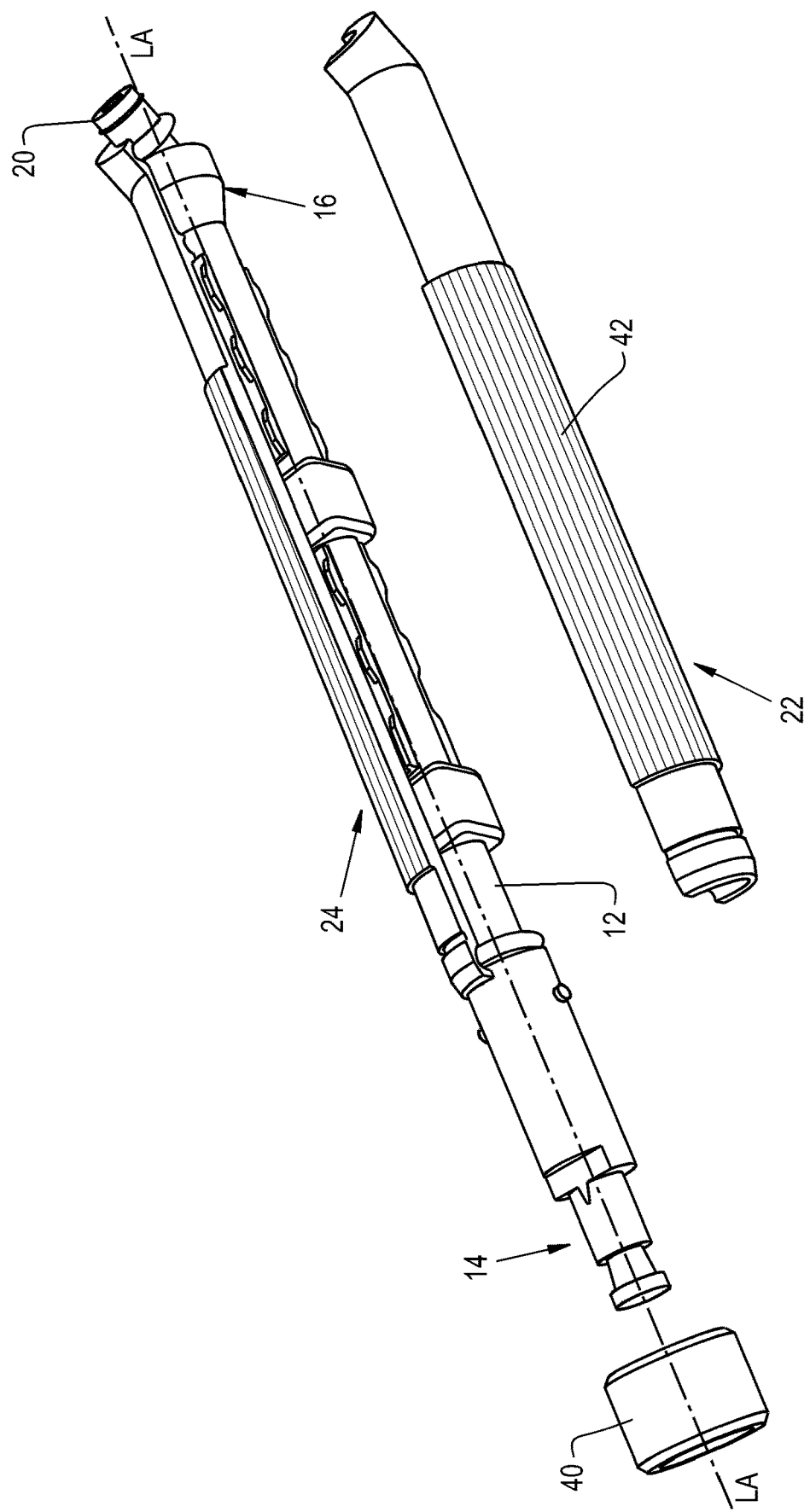

Referring now to FIGS. 5-7, there is shown an orthopaedic driver handle 10 according to the present invention as it undergoes disassembly. FIG. 5 shows the beginning step of removing the annular collar 44, which frees the first portion 22 and the section portion 24 to move in a direction of the longitudinal axis LA, with such sliding illustrated by arrows. FIG. 6 illustrates the step of distally sliding the first portion 22 in a direction of the longitudinal axis LA to disengage the locking protrusions 36 of the tabs 28 from the ramped features 34. Sliding the first portion 22 aligns the tabs 28 such that the locking protrusions 36 may pass outwardly along the bottom surface 26B of the grooves 26 between the ramped features 34. As shown in FIG. 6, the first portion 22 has been moved in a direction toward the instrument connector 20. FIG. 7 illustrates the step of separating the first portion 22 from the second portion 24. As long as the spacing between the ramped features 34 and locking protrusions 36 is suitably aligned, the first and second portions 22, 24 are free to separate from each other. Once the orthopaedic driver handle 10 is dissembled, it can be efficiently cleaned and reassembled.

Although the drawings of the present invention illustrate the orthopaedic driver handle 10 having the separable housing 18 with a circular cross-section, it is contemplated that the separable housing 18 can be made having any desired shape. For example, the separable housing 18 may have a rectangular or hexagonal cross-section. Additionally, the separable housing 18 is shown to be angled at one end, as defined by the angled axis AA, however the separable housing 18 may be composed of an entirely straight member or a member that has multiple angles and curves. Further, the first and second portions 22, 24 of the separable housing 18 may also connect to each other along an axis that is transverse to the longitudinal axis LA. For example, an embodiment of the separable housing 18 may be in the form of a multi-portion body that slides over a drive shaft, along the longitudinal axis LA, and connects by radially twisting or simply interlocking the portions along an axis that is perpendicular to the longitudinal axis LA.

While this invention has been described with respect to at least one embodiment, the present invention can be further modified within the spirit and scope of this disclosure. This application is therefore intended to cover any variations, uses, or adaptations of the invention using its general principles. Further, this application is intended to cover such departures from the present disclosure as come within known or customary practice in the art to which this invention pertains and which fall within the limits of the appended claims.

What is claimed is:

1. An orthopaedic driver handle, comprising:
   a drivetrain having a driving end and a driven end opposite said driving end and defining a longitudinal axis; and
   a separable housing covering at least a portion of said drivetrain, said separable housing including:
   a first portion and a second portion separably connected to the first portion, wherein sliding said first portion relative to said second portion in a direction of the longitudinal axis unlocks said first portion from said second portion, wherein said first portion includes an interior surface with at least one groove formed adjacent a peripheral edge of said first portion and said second portion includes at least one tab adjacent a peripheral edge of said second portion, said at least one tab extending circumferentially, relative to the longitudinal axis, past said peripheral edge of said second portion, each of said at least one groove adapted to separably receive each of said at least one tab, wherein a bottom surface defines a bottom of said at least one groove and at least two ramped features are positioned on said bottom surface, said at least one tab includes at least one locking protrusion extending radially, relative to the longitudinal axis, therefrom, wherein said at least one locking protrusion fits within said at least one groove and slidably aligns with at least one of said at least two ramped features to prevent said first portion and said second portion from being pulled apart, said at least two ramped features are spaced from each other to allow insertion of each of the at least one locking protrusion between the two ramped features.

2. The orthopaedic driver handle according to claim 1, wherein said first portion and said second portion each include an elongated region substantially parallel to the longitudinal axis and an angled region defining an angled axis relative to the longitudinal axis.

3. The orthopaedic driver handle according to claim 1, further including a first locking member mated to an exterior of said separable housing and adapted to prohibit sliding of said first portion relative to said second portion in the direction of the longitudinal axis.

4. The orthopaedic driver handle according to claim 3, wherein said first locking member is in the form of an annular collar.

5. The orthopaedic driver handle according to claim 3, wherein said first locking member includes a second locking member adapted to prevent said first locking member from sliding off said exterior of said separable housing.

6. The orthopaedic driver handle according to claim 5, wherein said second locking member is at least one of a spring-loaded element, a pin, a clasp, a thread and a fastener.

7. The orthopaedic driver handle according to claim 1, wherein said separable housing further includes a gripping feature on an outer surface of the separable housing in the form of at least one of a plurality of scallops, a gripping texture and at least one abrasion.

* * * * *